US012760284B2

(12) United States Patent
Michels et al.

(10) Patent No.: US 12,760,284 B2
(45) Date of Patent: Oct. 13, 2026

(54) STABLE SYNTHETIC PHYTASE VARIANTS

(71) Applicant: EW NUTRITION GMBH, Visbek (DE)

(72) Inventors: Andreas Michels, Düsseldorf (DE); Andreas Scheidig, Westoverledingen (DE); Thomas Horn, Hürth (DE); Alexander Metten, Cologne (DE)

(73) Assignee: EW NUTRITION GMBH, Visbek (DE)

( * ) Notice: Subject to any disclaimer, the term of this patent is extended or adjusted under 35 U.S.C. 154(b) by 531 days.

(21) Appl. No.: 18/036,967

(22) PCT Filed: Nov. 17, 2021

(86) PCT No.: PCT/EP2021/082016
§ 371 (c)(1),
(2) Date: May 15, 2023

(87) PCT Pub. No.: WO2022/106483
PCT Pub. Date: May 27, 2022

(65) Prior Publication Data

US 2023/0416702 A1 Dec. 28, 2023

(30) Foreign Application Priority Data

Nov. 17, 2020 (EP) .................................... 20208205

(51) Int. Cl.
*C12N 9/16* (2006.01)

(52) U.S. Cl.
CPC ........ *C12N 9/16* (2013.01); *C12Y 301/03008* (2013.01)

(58) Field of Classification Search
None
See application file for complete search history.

(56) References Cited

U.S. PATENT DOCUMENTS

| | | | |
|---|---|---|---|
| 8,557,555 B2 | 10/2013 | Haefner et al. | |
| 9,127,260 B2 | 9/2015 | Haefner et al. | |
| 2012/0201923 A1 | 8/2012 | Haefner et al. | |
| 2024/0174993 A1* | 5/2024 | Babe | A23K 20/189 |

FOREIGN PATENT DOCUMENTS

| | | | |
|---|---|---|---|
| CN | 102575237 | A | 7/2012 |
| CN | 103502443 | A | 1/2014 |
| CN | 103687944 | A | 3/2014 |
| EP | 16176044.2 | | 6/2016 |
| EP | 16206367.1 | | 12/2016 |
| JP | 2008-516597 | A2 | 4/2006 |
| JP | 2008-515401 | A | 11/2007 |
| JP | 2010-522548 | A | 1/2010 |
| JP | 2014-513944 | A | 6/2014 |
| WO | WO2011048046 | A2 | 4/2011 |
| WO | 2012/143861 | A1 | 10/2012 |
| WO | 2017/220776 | A1 | 12/2017 |
| WO | 2020-106796 | A | 5/2020 |
| WO | 2020/106796 | A1 | 5/2020 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Bornscheuer et al. Curr Protoc Protein Sci. Nov. 2011;Chapter 26:Unit26.7. (Year: 2011).*
Yoshikuni et al. Curr Opin Chem Biol. Apr. 2007;11(2):233-9. (Year: 2007).*
Accession A0A1C6YW96. Nov. 2, 2016 (Year: 2016).*
Ping Yu, et al.; "Codon optimisation improves the expression of *Trichoderma viride* sp. endochitinase in Pichia pastoris."; Sci Rep 3, 3043 (Oct. 24, 2013). https://doi.org/10.1038/srep03043.
Rosemary A. Cripwell, et al.; "Expression and comparison of codon optimised Aspergillus tubingensis amylase variants in *Saccharomyces cerevisiae*", FEMS Yeast Research, vol. 17, Issue 4, Jun. 2017, fox040.
Carola Engler, et al.; "Golden Gate Shuffling: A One-Pot DNA Shuffling Method Based on Type IIs Restriction Enzymes."; PLoS ONE May 2009, vol. 4(5): e5553.
Partridge G; "New generation phytase with high thermostability"; Pig Progress, vol. 23, No. 4, Jan. 5, 2007.
Kevin R. Herrmann, et al.; "Engineered phytases for emerging biotechnological applications beyond animal feeding." Applied Microbiology Biotechnology vol. 103, No. 16, Jun. 28, 2019.
Sharrel Rebello, et al; "Molecular advancements in the development of thermostable phytases."; Applied Microbiology Biotechnology , vol. 101, No. 7, Feb. 23, 2017.
Jinlong Bei, et al.; "Structure-based fragment shuffling of two fungal phytases for combination of desirable properties." Journal of Biotechnology. vol. 139(2), Jan. 15, 2009.
Jiangke Yang, et al.; "Codon optimization through a two-step gene synthesis leads to a high-level expression of Aspergillus niger lip2 gene in Pichia pastoris."; Journal of Molecular Catalysis B-enzymatic 63 (May 2010) abstract.
International Search Report dated Feb. 23, 2022, for corresponding International Patent Application No. PCT/EP2021/082016.
Written Opinion of the International Preliminary Examining Authority dated Feb. 23, 2022, for corresponding International Patent Application No. PCT/EP2021/082016.
International Preliminary Report On Patentability dated Mar. 7, 2023, for corresponding International Patent Application No. PCT/EP2021/082016.
Annexure to International Preliminary Report On Patentability dated Mar. 7, 2023, for corresponding International Patent Application No. PCT/EP2021/082016.

(Continued)

*Primary Examiner* — Christian L Fronda
(74) *Attorney, Agent, or Firm* — Meunier Carlin & Curfman LLC

(57) ABSTRACT

The present invention relates to a synthetic phytase which is a shuffling product comprising biobricks of at least two reference phytases of *Obesumbacterium* and/or *Hafnia*.

12 Claims, 6 Drawing Sheets

Specification includes a Sequence Listing.

(56) References Cited

OTHER PUBLICATIONS

Office Action issued by the Japanese Application No. 2023-528946 mailed Oct. 30, 2025, 4 pages.
First Office Action issued by the Chinese Application No. 2023-528946 mailed Jun. 26, 2026, 10 pages.
English Translation of First Office Action issued by the Chinese Application No. 2023-528946 mailed Jun. 26, 2026, 10 pages.

* cited by examiner

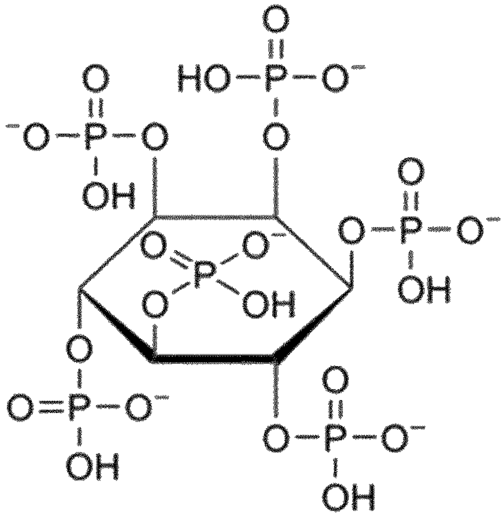
Fig. 1: Phytate
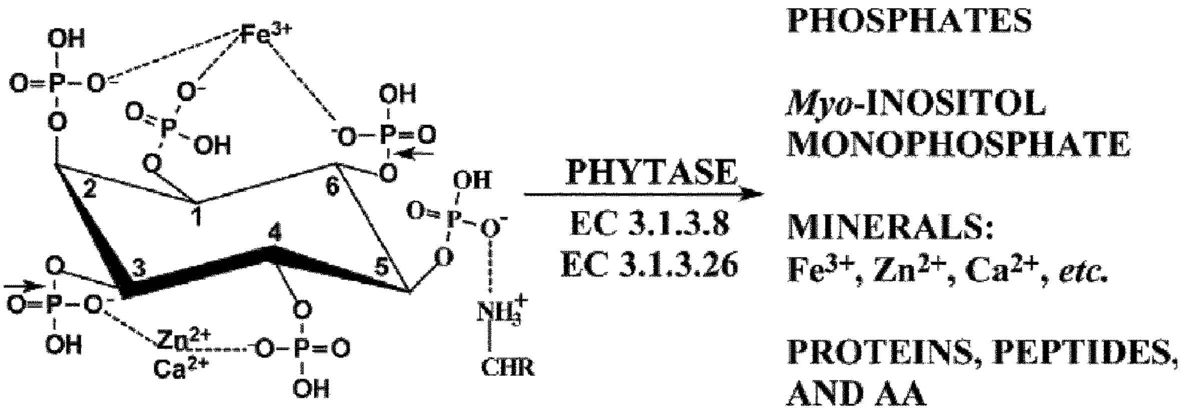
Fig. 2: Phytase reaction

| Name | Short name | SEQ ID NO | pH-Profile (activity > 50 %) | pH optimum | IT50 (10 min) °C | % pH 2.5 resistance | Pepsin-resistance % | K1 resistance (700U) % | K1 resistance (6000U)% |
|---|---|---|---|---|---|---|---|---|---|
| *Obesumbacterium/ Hafnia/ Obesumbacterium* | O/H/O | 3 | 2,5-5,5 | 4 | 65,4 | 111% | 103% | 105% | 110% |
| *Hafnia/Hafnia/ Obesumbacterium* | H/H/O | 4 | 2,0-5,5 | 4,5 | 64,4 | 107% | 76% | 105% | 106% |
| *Obesumbacterium/ Hafnia/Hafnia* | O/H/H | 5 | 2,0-5,5 | 4,5 | 64,3 | 112% | 105% | 106% | 109% |
| *wildtype Hafnia alvei* | *H. alvei* | 1 | 2,5-5,5 | 4,5 | 63,2 | 96% | 99% | 83% | 84% |
| *wildtype Obesumbacterium proteus* | *O. proteus* | 2 | 2,5-5,5 | 4 | 60,4 | 110% | 118% | 99% | 93% |

Fig. 3

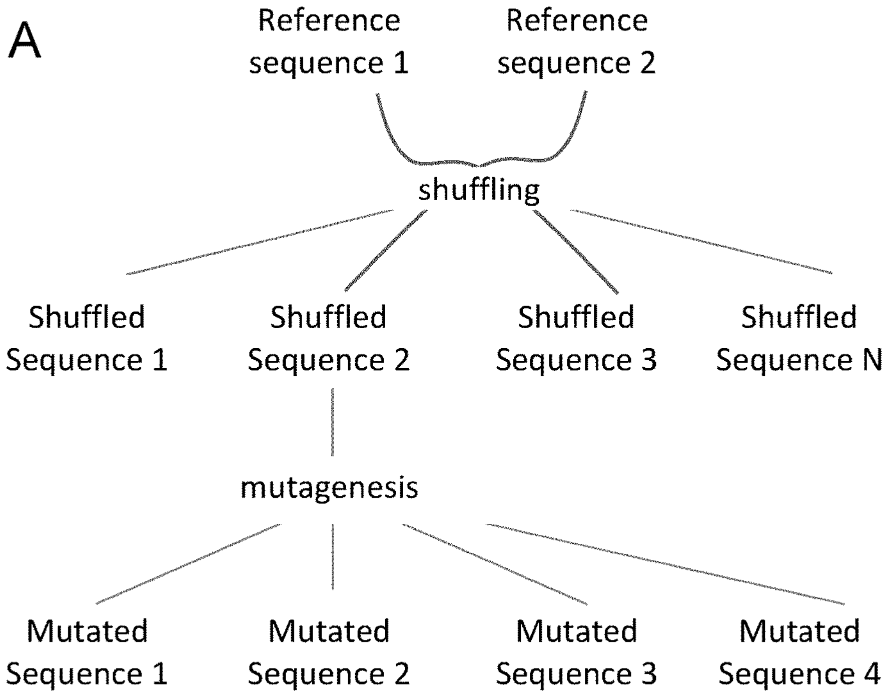

Fig. 4

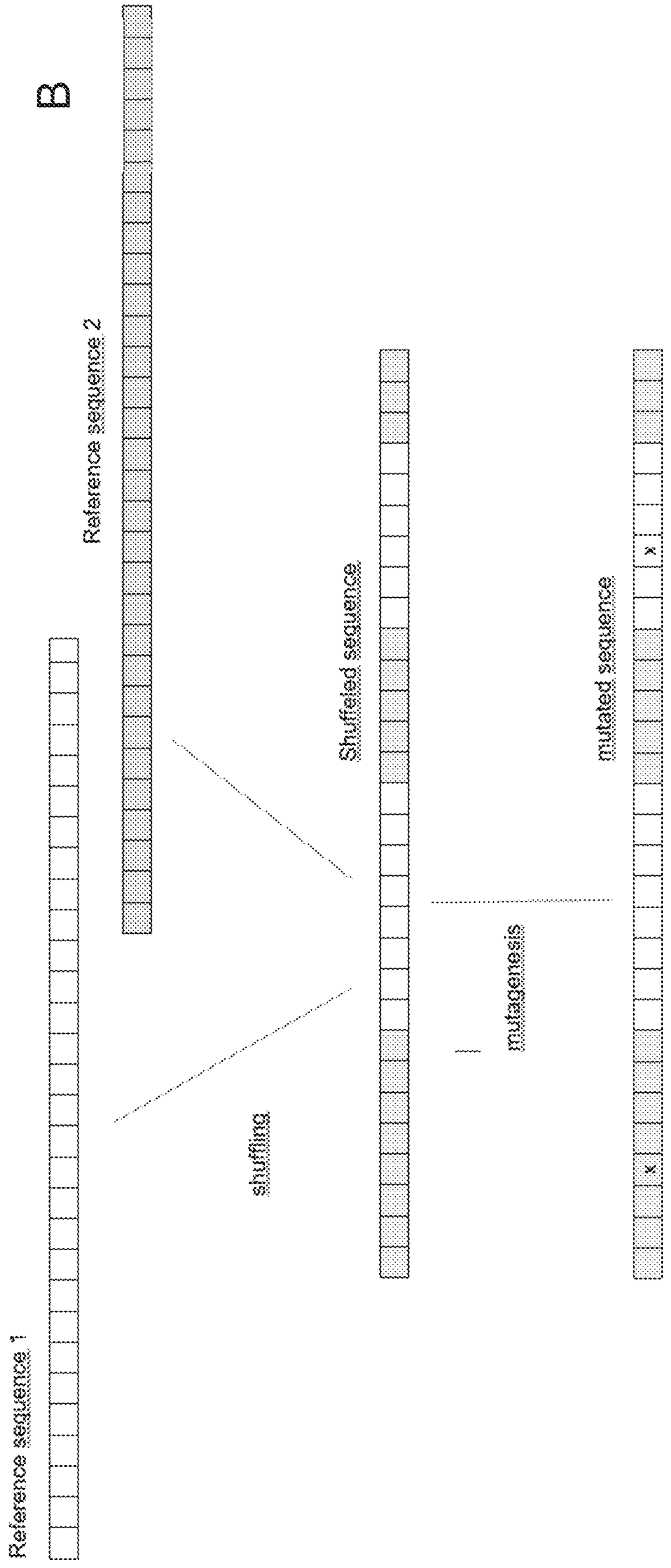
Fig. 4cont'd

```
Hafnia       1 SDTAPAGFQLEKVVILSRHGVRAPTKMTQTMRNVTPHQWPEWPVKLGYIT  50
               |:|.|:|:||||||||||||||||||||||||:|||:.||||||||||||
Obesum       1 SETVPSGYQLEKVVILSRHGVRAPTKMTQTMRDVTPNTWPEWPVKLGYIT  50

Hafnia      51 PRGEHLISLMGGFYRERFQQQGLLPKDNCPTPDAVYVWADVDQRTRKTGE 100
               ||||||:||||||||::|||.|:|.||.|||.:.||||||||||||||||
Obesum      51 PRGEHLVSLMGGFYRQKFQQLGILSKDRCPTANDVYVWADVDQRTRKTGE 100

Hafnia     101 AFLAGLAPQCDLAIHHQQNIQQADPLFHPVKAGICSMDKSQAHAAVEKQA 150
               ||||||||:|.|:|||||:|:|.|.||||||||:|:|:|:|...|||:||
Obesum     101 AFLAGLAPECHLSIHHQQDIKQVDSLFHPVKAGVCTMEKAQVQQAVEQQA 150

Hafnia     151 GTPIETLNQRYQASLALMSSVLDFPKSPYCQQHNIGKLCDFSQAMPSRLA 200
               |.||..|||.|:.:|||||:||:||.|.|||||:..:.|:|::.|||:|:
Obesum     151 GMPIAQLNQHYRPALALMSNVLNFPTSAYCQQHSAEQTCNFAEVMPSKLS 200

Hafnia     201 INDDGNKVALEGAVGLSSTLAEIFLLEHAQGMPKVAWGNIHTEQQWDSLL 250
               |.||||||||:||||||||||||||||||||||..|||.||:||.|::||
Obesum     201 IKDDGNKVALDGAVGLSSTLAEIFLLEHAQGMPNAAWGKIHSEQDWNTLL 250

Hafnia     251 KLHNAQFDLMSRTPYIAKHNGTPLLQTIAHALGSNIASRPLPDISPDNKI 300
               .|||||||||||||||||||||||||||..|:.|..:.|.||::|.||||
Obesum     251 TLHNAQFDLMSRTPYIAKHNGTPLLQTIVSAINSQTSPRELPELSADNKI 300

Hafnia     301 LFIAGHDTNIANISGMLGMTWTLPGQPDNTPPGGALVFERWVDNAGKPYV 350
               ||:||||||||||:||||::|||||||||||||||||||||.|..||.||
Obesum     301 LFLAGHDTNIANIAGMLGLSWTLPGQPDNTPPGGALVFERWSDKTGKKYV 350

Hafnia     351 SVNMVYQTLAQLHDQTPLTLQHPAGSVRLNIPGCSDQTPDGYCPLSTFSR 400
               |..|:|||||||.:||||||..|||||.|.||||.|||.:|||||.||:|
Obesum     351 SAQMMYQTLAQLRNQTPLTLDEPAGSVALKIPGCDDQTAEGYCPLDTFTR 400

Hafnia     401 LVNHSVEPACQLP    413
               |...:....||
Obesum     401 LAKQNELAECQ--    411
```

Fig. 5

```
Hafnia       1 SDTAPAGFQLEKVVILSRHGVRAPTKMTQTMRNVTPHQWPEWPVKLGYIT   50
               |:|.|:|:||||||||||||||||||||||||:|||:.||||||||||||
OHO          1 SETVPSGYQLEKVVILSRHGVRAPTKMTQTMRDVTPNTWPEWPVKLGYIT   50

Hafnia      51 PRGEHLISLMGGFYRERFQQQGLLPKDNCPTPDAVYVWADVDQRTRKTGE  100
               ||||||:||||||||::|||.|:|.||.|||.:.||||||||||||||||
OHO         51 PRGEHLVSLMGGFYRQKFQQLGILSKDRCPTANDVYVWADVDQRTRKTGE  100

Hafnia     101 AFLAGLAPQCDLAIHHQQNIQQADPLFHPVKAGICSMDKSQAHAAVEKQA  150
               ||||||||||||||||||||||||||||||||||||||||||||||||||
OHO        101 AFLAGLAPQCDLAIHHQQNIQQADPLFHPVKAGICSMDKSQAHAAVEKQA  150

Hafnia     151 GTPIETLNQRYQASLALMSSVLDFPKSPYCQQHNIGKLCDFSQAMPSRLA  200
               ||||||||||||||||||||||||||||||||||||||||||||||||||
OHO        151 GTPIETLNQRYQASLALMSSVLDFPKSPYCQQHNIGKLCDFSQAMPSRLA  200

Hafnia     201 INDDGNKVALEGAVGLSSTLAEIFLLEHAQGMPKVAWGNIHTEQQWDSLL  250
               ||||||||||||||||||||||||||||||||||||||||||||||||||
OHO        201 INDDGNKVALEGAVGLSSTLAEIFLLEHAQGMPKVAWGNIHTEQQWDSLL  250

Hafnia     251 KLHNAQFDLMSRTPYIAKHNGTPLLQTIAHALGSNIASRPLPDISPDNKI  300
               ||||||||||||||||||||||||||||..|:.|..:.|.||::|.||||
OHO        251 KLHNAQFDLMSRTPYIAKHNGTPLLQTIVSAINSQTSPRELPELSADNKI  300

Hafnia     301 LFIAGHDTNIANISGMLGMTWTLPGQPDNTPPGGALVFERWVDNAGKPYV  350
               ||:||||||||||:||||::|||||||||||||||||||||.|..||.||
OHO        301 LFLAGHDTNIANIAGMLGLSWTLPGQPDNTPPGGALVFERWSDKTGKKYV  350

Hafnia     351 SVNMVYQTLAQLHDQTPLTLQHPAGSVRLNIPGCSDQTPDGYCPLSTFSR  400
               |..|:|||||||.:||||||..|||||.|.||||.|||.:|||||.||:|
OHO        351 SAQMMYQTLAQLRNQTPLTLDEPAGSVALKIPGCDDQTAEGYCPLDTFTR  400

Hafnia     401 LVNHSVEPACQLP    413
               |...:....||
OHO        401 LAKQNELAECQ--    411
```

Fig. 6

SEQUENCE LISTING

```
<160> NUMBER OF SEQ ID NOS: 5

<210> SEQ ID NO 1
<211> LENGTH: 413
<212> TYPE: PRT
<213> ORGANISM: Hafnia alvei

<400> SEQUENCE: 1

Ser Asp Thr Ala Pro Ala Gly Phe Gln Leu Glu Lys Val Val Ile Leu
1               5                   10                  15

Ser Arg His Gly Val Arg Ala Pro Thr Lys Met Thr Gln Thr Met Arg
            20                  25                  30

Asn Val Thr Pro His Gln Trp Pro Glu Trp Pro Val Lys Leu Gly Tyr
        35                  40                  45

Ile Thr Pro Arg Gly Glu His Leu Ile Ser Leu Met Gly Gly Phe Tyr
    50                  55                  60

Arg Glu Arg Phe Gln Gln Gln Gly Leu Leu Pro Lys Asp Asn Cys Pro
65                  70                  75                  80

Thr Pro Asp Ala Val Tyr Val Trp Ala Asp Val Asp Gln Arg Thr Arg
                85                  90                  95

Lys Thr Gly Glu Ala Phe Leu Ala Gly Leu Ala Pro Gln Cys Asp Leu
            100                 105                 110

Ala Ile His His Gln Gln Asn Ile Gln Gln Ala Asp Pro Leu Phe His
        115                 120                 125

Pro Val Lys Ala Gly Ile Cys Ser Met Asp Lys Ser Gln Ala His Ala
    130                 135                 140

Ala Val Glu Lys Gln Ala Gly Thr Pro Ile Glu Thr Leu Asn Gln Arg
145                 150                 155                 160

Tyr Gln Ala Ser Leu Ala Leu Met Ser Ser Val Leu Asp Phe Pro Lys
                165                 170                 175

Ser Pro Tyr Cys Gln Gln His Asn Ile Gly Lys Leu Cys Asp Phe Ser
            180                 185                 190

Gln Ala Met Pro Ser Arg Leu Ala Ile Asn Asp Asp Gly Asn Lys Val
        195                 200                 205

Ala Leu Glu Gly Ala Val Gly Leu Ser Ser Thr Leu Ala Glu Ile Phe
    210                 215                 220
```

```
Leu Leu Glu His Ala Gln Gly Met Pro Lys Val Ala Trp Gly Asn Ile
225                 230                 235                 240

His Thr Glu Gln Gln Trp Asp Ser Leu Leu Lys Leu His Asn Ala Gln
                245                 250                 255

Phe Asp Leu Met Ser Arg Thr Pro Tyr Ile Ala Lys His Asn Gly Thr
            260                 265                 270

Pro Leu Leu Gln Thr Ile Ala His Ala Leu Gly Ser Asn Ile Ala Ser
        275                 280                 285

Arg Pro Leu Pro Asp Ile Ser Pro Asp Asn Lys Ile Leu Phe Ile Ala
    290                 295                 300

Gly His Asp Thr Asn Ile Ala Asn Ile Ser Gly Met Leu Gly Met Thr
305                 310                 315                 320

Trp Thr Leu Pro Gly Gln Pro Asp Asn Thr Pro Pro Gly Gly Ala Leu
                325                 330                 335

Val Phe Glu Arg Trp Val Asp Asn Ala Gly Lys Pro Tyr Val Ser Val
            340                 345                 350

Asn Met Val Tyr Gln Thr Leu Ala Gln Leu His Asp Gln Thr Pro Leu
        355                 360                 365

Thr Leu Gln His Pro Ala Gly Ser Val Arg Leu Asn Ile Pro Gly Cys
    370                 375                 380

Ser Asp Gln Thr Pro Asp Gly Tyr Cys Pro Leu Ser Thr Phe Ser Arg
385                 390                 395                 400

Leu Val Asn His Ser Val Glu Pro Ala Cys Gln Leu Pro
                405                 410


<210> SEQ ID NO 2
<211> LENGTH: 411
<212> TYPE: PRT
<213> ORGANISM: Obesumbacterium

<400> SEQUENCE: 2

Ser Glu Thr Val Pro Ser Gly Tyr Gln Leu Glu Lys Val Val Ile Leu
1               5                   10                  15

Ser Arg His Gly Val Arg Ala Pro Thr Lys Met Thr Gln Thr Met Arg
            20                  25                  30

Asp Val Thr Pro Asn Thr Trp Pro Glu Trp Pro Val Lys Leu Gly Tyr
        35                  40                  45

Ile Thr Pro Arg Gly Glu His Leu Val Ser Leu Met Gly Gly Phe Tyr
    50                  55                  60

Arg Gln Lys Phe Gln Gln Leu Gly Ile Leu Ser Lys Asp Arg Cys Pro
65                  70                  75                  80

Thr Ala Asn Asp Val Tyr Val Trp Ala Asp Val Asp Gln Arg Thr Arg
                85                  90                  95

Lys Thr Gly Glu Ala Phe Leu Ala Gly Leu Ala Pro Glu Cys His Leu
            100                 105                 110

Ser Ile His His Gln Gln Asp Ile Lys Gln Val Asp Ser Leu Phe His
        115                 120                 125

Pro Val Lys Ala Gly Val Cys Thr Met Glu Lys Ala Gln Val Gln Gln
    130                 135                 140

Ala Val Glu Gln Gln Ala Gly Met Pro Ile Ala Gln Leu Asn Gln His
145                 150                 155                 160

Tyr Arg Pro Ala Leu Ala Leu Met Ser Asn Val Leu Asn Phe Pro Thr
                165                 170                 175

Ser Ala Tyr Cys Gln Gln His Ser Ala Glu Gln Thr Cys Asn Phe Ala
```

```
            180                 185                 190

Glu Val Met Pro Ser Lys Leu Ser Ile Lys Asp Asp Gly Asn Lys Val
        195                 200                 205

Ala Leu Asp Gly Ala Val Gly Leu Ser Ser Thr Leu Ala Glu Ile Phe
    210                 215                 220

Leu Leu Glu His Ala Gln Gly Met Pro Asn Ala Ala Trp Gly Lys Ile
225                 230                 235                 240

His Ser Glu Gln Asp Trp Asn Thr Leu Leu Thr Leu His Asn Ala Gln
                245                 250                 255

Phe Asp Leu Met Ser Arg Thr Pro Tyr Ile Ala Lys His Asn Gly Thr
            260                 265                 270

Pro Leu Leu Gln Thr Ile Val Ser Ala Ile Asn Ser Gln Thr Ser Pro
        275                 280                 285

Arg Glu Leu Pro Glu Leu Ser Ala Asp Asn Lys Ile Leu Phe Leu Ala
    290                 295                 300

Gly His Asp Thr Asn Ile Ala Asn Ile Ala Gly Met Leu Gly Leu Ser
305                 310                 315                 320

Trp Thr Leu Pro Gly Gln Pro Asp Asn Thr Pro Pro Gly Gly Ala Leu
                325                 330                 335

Val Phe Glu Arg Trp Ser Asp Lys Thr Gly Lys Lys Tyr Val Ser Ala
            340                 345                 350

Gln Met Met Tyr Gln Thr Leu Ala Gln Leu Arg Asn Gln Thr Pro Leu
        355                 360                 365

Thr Leu Asp Glu Pro Ala Gly Ser Val Ala Leu Lys Ile Pro Gly Cys
    370                 375                 380

Asp Asp Gln Thr Ala Glu Gly Tyr Cys Pro Leu Asp Thr Phe Thr Arg
385                 390                 395                 400

Leu Ala Lys Gln Asn Glu Leu Ala Glu Cys Gln
                405                 410


<210> SEQ ID NO 3
<211> LENGTH: 411
<212> TYPE: PRT
<213> ORGANISM: artificial sequence
<220> FEATURE:
<223> OTHER INFORMATION: shuffled variant

<400> SEQUENCE: 3

Ser Glu Thr Val Pro Ser Gly Tyr Gln Leu Glu Lys Val Val Ile Leu
1               5                   10                  15

Ser Arg His Gly Val Arg Ala Pro Thr Lys Met Thr Gln Thr Met Arg
            20                  25                  30

Asp Val Thr Pro Asn Thr Trp Pro Glu Trp Pro Val Lys Leu Gly Tyr
        35                  40                  45

Ile Thr Pro Arg Gly Glu His Leu Val Ser Leu Met Gly Gly Phe Tyr
    50                  55                  60

Arg Gln Lys Phe Gln Gln Leu Gly Ile Leu Ser Lys Asp Arg Cys Pro
65                  70                  75                  80

Thr Ala Asn Asp Val Tyr Val Trp Ala Asp Val Asp Gln Arg Thr Arg
                85                  90                  95

Lys Thr Gly Glu Ala Phe Leu Ala Gly Leu Ala Pro Gln Cys Asp Leu
            100                 105                 110

Ala Ile His His Gln Gln Asn Ile Gln Gln Ala Asp Pro Leu Phe His
        115                 120                 125

Pro Val Lys Ala Gly Ile Cys Ser Met Asp Lys Ser Gln Ala His Ala
```

```
    130                 135                 140

Ala Val Glu Lys Gln Ala Gly Thr Pro Ile Glu Thr Leu Asn Gln Arg
145                 150                 155                 160

Tyr Gln Ala Ser Leu Ala Leu Met Ser Ser Val Leu Asp Phe Pro Lys
                165                 170                 175

Ser Pro Tyr Cys Gln Gln His Asn Ile Gly Lys Leu Cys Asp Phe Ser
            180                 185                 190

Gln Ala Met Pro Ser Arg Leu Ala Ile Asn Asp Asp Gly Asn Lys Val
        195                 200                 205

Ala Leu Glu Gly Ala Val Gly Leu Ser Ser Thr Leu Ala Glu Ile Phe
    210                 215                 220

Leu Leu Glu His Ala Gln Gly Met Pro Lys Val Ala Trp Gly Asn Ile
225                 230                 235                 240

His Thr Glu Gln Gln Trp Asp Ser Leu Leu Lys Leu His Asn Ala Gln
                245                 250                 255

Phe Asp Leu Met Ser Arg Thr Pro Tyr Ile Ala Lys His Asn Gly Thr
            260                 265                 270

Pro Leu Leu Gln Thr Ile Val Ser Ala Ile Asn Ser Gln Thr Ser Pro
        275                 280                 285

Arg Glu Leu Pro Glu Leu Ser Ala Asp Asn Lys Ile Leu Phe Leu Ala
    290                 295                 300

Gly His Asp Thr Asn Ile Ala Asn Ile Ala Gly Met Leu Gly Leu Ser
305                 310                 315                 320

Trp Thr Leu Pro Gly Gln Pro Asp Asn Thr Pro Pro Gly Gly Ala Leu
                325                 330                 335

Val Phe Glu Arg Trp Ser Asp Lys Thr Gly Lys Lys Tyr Val Ser Ala
            340                 345                 350

Gln Met Met Tyr Gln Thr Leu Ala Gln Leu Arg Asn Gln Thr Pro Leu
        355                 360                 365

Thr Leu Asp Glu Pro Ala Gly Ser Val Ala Leu Lys Ile Pro Gly Cys
    370                 375                 380

Asp Asp Gln Thr Ala Glu Gly Tyr Cys Pro Leu Asp Thr Phe Thr Arg
385                 390                 395                 400

Leu Ala Lys Gln Asn Glu Leu Ala Glu Cys Gln
                405                 410


<210> SEQ ID NO 4
<211> LENGTH: 411
<212> TYPE: PRT
<213> ORGANISM: artificial sequence
<220> FEATURE:
<223> OTHER INFORMATION: shuffled variant

<400> SEQUENCE: 4

Ser Asp Thr Ala Pro Ala Gly Phe Gln Leu Glu Lys Val Val Ile Leu
1               5                   10                  15

Ser Arg His Gly Val Arg Ala Pro Thr Lys Met Thr Gln Thr Met Arg
            20                  25                  30

Asn Val Thr Pro His Gln Trp Pro Glu Trp Pro Val Lys Leu Gly Tyr
        35                  40                  45

Ile Thr Pro Arg Gly Glu His Leu Ile Ser Leu Met Gly Gly Phe Tyr
    50                  55                  60

Arg Glu Arg Phe Gln Gln Gln Gly Leu Leu Pro Lys Asp Asn Cys Pro
65                  70                  75                  80

Thr Pro Asp Ala Val Tyr Val Trp Ala Asp Val Asp Gln Arg Thr Arg
```

```
                85                  90                  95

Lys Thr Gly Glu Ala Phe Leu Ala Gly Leu Ala Pro Gln Cys Asp Leu
            100                 105                 110

Ala Ile His His Gln Gln Asn Ile Gln Gln Ala Asp Pro Leu Phe His
        115                 120                 125

Pro Val Lys Ala Gly Ile Cys Ser Met Asp Lys Ser Gln Ala His Ala
    130                 135                 140

Ala Val Glu Lys Gln Ala Gly Thr Pro Ile Glu Thr Leu Asn Gln Arg
145                 150                 155                 160

Tyr Gln Ala Ser Leu Ala Leu Met Ser Ser Val Leu Asp Phe Pro Lys
                165                 170                 175

Ser Pro Tyr Cys Gln Gln His Asn Ile Gly Lys Leu Cys Asp Phe Ser
            180                 185                 190

Gln Ala Met Pro Ser Arg Leu Ala Ile Asn Asp Asp Gly Asn Lys Val
        195                 200                 205

Ala Leu Glu Gly Ala Val Gly Leu Ser Ser Thr Leu Ala Glu Ile Phe
    210                 215                 220

Leu Leu Glu His Ala Gln Gly Met Pro Lys Val Ala Trp Gly Asn Ile
225                 230                 235                 240

His Thr Glu Gln Gln Trp Asp Ser Leu Leu Lys Leu His Asn Ala Gln
                245                 250                 255

Phe Asp Leu Met Ser Arg Thr Pro Tyr Ile Ala Lys His Asn Gly Thr
            260                 265                 270

Pro Leu Leu Gln Thr Ile Val Ser Ala Ile Asn Ser Gln Thr Ser Pro
        275                 280                 285

Arg Glu Leu Pro Glu Leu Ser Ala Asp Asn Lys Ile Leu Phe Leu Ala
    290                 295                 300

Gly His Asp Thr Asn Ile Ala Asn Ile Ala Gly Met Leu Gly Leu Ser
305                 310                 315                 320

Trp Thr Leu Pro Gly Gln Pro Asp Asn Thr Pro Pro Gly Gly Ala Leu
                325                 330                 335

Val Phe Glu Arg Trp Ser Asp Lys Thr Gly Lys Lys Tyr Val Ser Ala
            340                 345                 350

Gln Met Met Tyr Gln Thr Leu Ala Gln Leu Arg Asn Gln Thr Pro Leu
        355                 360                 365

Thr Leu Asp Glu Pro Ala Gly Ser Val Ala Leu Lys Ile Pro Gly Cys
    370                 375                 380

Asp Asp Gln Thr Ala Glu Gly Tyr Cys Pro Leu Asp Thr Phe Thr Arg
385                 390                 395                 400

Leu Ala Lys Gln Asn Glu Leu Ala Glu Cys Gln
                405                 410


<210> SEQ ID NO 5
<211> LENGTH: 413
<212> TYPE: PRT
<213> ORGANISM: artificial sequence
<220> FEATURE:
<223> OTHER INFORMATION: shuffled variant

<400> SEQUENCE: 5

Ser Glu Thr Val Pro Ser Gly Tyr Gln Leu Glu Lys Val Val Ile Leu
1               5                   10                  15

Ser Arg His Gly Val Arg Ala Pro Thr Lys Met Thr Gln Thr Met Arg
            20                  25                  30

Asp Val Thr Pro Asn Thr Trp Pro Glu Trp Pro Val Lys Leu Gly Tyr
```

-continued

```
        35                  40                  45

Ile Thr Pro Arg Gly Glu His Leu Val Ser Leu Met Gly Gly Phe Tyr
    50                  55                  60

Arg Gln Lys Phe Gln Gln Leu Gly Ile Leu Ser Lys Asp Arg Cys Pro
65                  70                  75                  80

Thr Ala Asn Asp Val Tyr Val Trp Ala Asp Val Asp Gln Arg Thr Arg
                85                  90                  95

Lys Thr Gly Glu Ala Phe Leu Ala Gly Leu Ala Pro Gln Cys Asp Leu
            100                 105                 110

Ala Ile His His Gln Gln Asn Ile Gln Gln Ala Asp Pro Leu Phe His
        115                 120                 125

Pro Val Lys Ala Gly Ile Cys Ser Met Asp Lys Ser Gln Ala His Ala
    130                 135                 140

Ala Val Glu Lys Gln Ala Gly Thr Pro Ile Glu Thr Leu Asn Gln Arg
145                 150                 155                 160

Tyr Gln Ala Ser Leu Ala Leu Met Ser Ser Val Leu Asp Phe Pro Lys
                165                 170                 175

Ser Pro Tyr Cys Gln Gln His Asn Ile Gly Lys Leu Cys Asp Phe Ser
            180                 185                 190

Gln Ala Met Pro Ser Arg Leu Ala Ile Asn Asp Asp Gly Asn Lys Val
        195                 200                 205

Ala Leu Glu Gly Ala Val Gly Leu Ser Ser Thr Leu Ala Glu Ile Phe
    210                 215                 220

Leu Leu Glu His Ala Gln Gly Met Pro Lys Val Ala Trp Gly Asn Ile
225                 230                 235                 240

His Thr Glu Gln Gln Trp Asp Ser Leu Leu Lys Leu His Asn Ala Gln
                245                 250                 255

Phe Asp Leu Met Ser Arg Thr Pro Tyr Ile Ala Lys His Asn Gly Thr
            260                 265                 270

Pro Leu Leu Gln Thr Ile Ala His Ala Leu Gly Ser Asn Ile Ala Ser
        275                 280                 285

Arg Pro Leu Pro Asp Ile Ser Pro Asp Asn Lys Ile Leu Phe Ile Ala
    290                 295                 300

Gly His Asp Thr Asn Ile Ala Asn Ile Ser Gly Met Leu Gly Met Thr
305                 310                 315                 320

Trp Thr Leu Pro Gly Gln Pro Asp Asn Thr Pro Pro Gly Gly Ala Leu
                325                 330                 335

Val Phe Glu Arg Trp Val Asp Asn Ala Gly Lys Pro Tyr Val Ser Val
            340                 345                 350

Asn Met Val Tyr Gln Thr Leu Ala Gln Leu His Asp Gln Thr Pro Leu
        355                 360                 365

Thr Leu Gln His Pro Ala Gly Ser Val Arg Leu Asn Ile Pro Gly Cys
    370                 375                 380

Ser Asp Gln Thr Pro Asp Gly Tyr Cys Pro Leu Ser Thr Phe Ser Arg
385                 390                 395                 400

Leu Val Asn His Ser Val Glu Pro Ala Cys Gln Leu Pro
                405                 410
```

STABLE SYNTHETIC PHYTASE VARIANTS

This application is a National Stage Application under 35 U.S.C. § 371 of PCT International Application No. PCT/EP2021/082016, filed on Nov. 17, 2021, which claims priority to European Patent Application No. EP 20208205.3, filed Nov. 17, 2020, all of which are hereby incorporated by reference herein in their entireties.

FIELD OF THE INVENTION

The present invention relates to the field of phytases.

BACKGROUND

Phytases (myo-inositol hexakisphosphate phosphohydrolase) are phosphatase enzymes that catalyze the hydrolysis of phytic acid (myo-inositol hexakisphosphate)—an indigestible, organic form of phosphorus that is found in grains and oil seeds—and releases a usable form of inorganic phosphorus. Phytases have been found to occur in animals, plants, fungi and bacteria. Phytases used in feed applications were initially of fungal origin but today are dominated by bacterial enzymes. Phytases can be grouped based on their pH activity optima, as acid or alkaline phytases, their catalytic mechanism and enzyme fold, as histidine acid, cysteine, or purple acid phosphatases, or B-propeller phytases, or by the stereoselectivity of phytate degradation as 3- or 6-phytase. The EC database accounts for this stereoselectivity by defining two classes, 3.1.3.8 and 3.1.3.26, the two classes that are used commercially. Phytases belonging to the group 3.1.3.72 (PTP-like phytases) and 3.1.3.2 (purple acid phosphatase) are rare and not exploited commercially.

Phytic acid and its metabolites have several important roles in seeds and grains, most notably, phytic acid functions as a phosphorus store, as an energy store, as a source of cations and as a source of myo-inositol (a cell wall precursor). Phytic acid is the principal storage form of phosphorus in plant seeds and the major source of phosphorus in the grain-based diets used in intensive livestock operations. The organic phosphate found in phytic acid is largely unavailable to the animals that consume it, but the inorganic phosphate that phytases release can be easily absorbed. Ruminant animals can use phytic acid as a source of phosphorus because the bacteria that inhabit their gut are well-characterized producers of many types of phytases.

However, monogastric animals cannot use phytic acid as a major source of phosphorus, due to a lack of sufficient amount of phytase produced by the gastro intestinal microbiota, and it is excreted in the feces.

In ruminants (cattle, sheep), phytase is produced by bacteria found in the gut making it possible for them to use the phytic acid found in grains as a source of phosphorus. Non-ruminants (monogastric animals) like humans, dogs, birds, etc. do not produce phytase. Research in the field of animal nutrition has put forth the idea of supplementing feed with phytase so as to make available to the animal phytate-bound nutrients like calcium, phosphorus, other minerals, carbohydrates, and proteins.

Phytase is used as an animal feed supplement—often in poultry and swine—to enhance the nutritive value of plant material by liberation of inorganic phosphate from phytic acid (myo-inositol hexakisphosphate). Phytase can be purified from transgenic microbes and has been produced recently in transgenic canola, alfalfa and rice plants. Phytase can also be produced on a large scale through cellulosic biomass fermentation using genetically modified (GM) yeast.

In many applications, improved stability of the enzyme is a significant advantage. Improved thermostability helps to increase the processability of the respective phytase, because the latter oftentimes undergoes thermal treatment during the manufacturing process.

This applies, inter alia, for the use of phytases in animal feed. During feed processing, the feed is often subjected to heat, e.g., by application of steam, to reduce or eliminate pathogens, increase storage life of the feed and optimized utilization of the ingredients leading to improved feed conversion. The conditioning time can vary from a few seconds up to several minutes depending on the type and formulation of the feed. The temperature during conditioning typically ranges from 70° C. to 100° C. After conditioning, the feed is sometimes extruded through a pelleting die, which for a short time raises the temperature of the feed incrementally due to heat dissipation caused by friction.

Yet in other applications, phytase enzymes are exposed to heat as well. Because phytases are proteins, they are susceptible to denaturation by heat and pressure. Denaturing essentially alters the structure of the enzyme, resulting in decreased activity levels and decreased efficacy of the enzyme.

There are different ways to improve phytase stability or protect phytases from thermal impact. In animal feed applications, one option is post-pellet liquid application, which is relatively complex and expensive because it requires the purchase and installation of specialized equipment, space in which to store the liquid enzyme and careful calculation of the amount of enzyme to apply.

Another option is the application of a protective coating before pelleting of the synthetic phytase with other ingredients (e.g., in feed). This approach, which is for example described in Partridge (2007), may reduce the efficacy of the enzyme because the coating may not fully dissolve, e.g., in the digestive tract of the animal. It is furthermore difficult to achieve a coating design that can withstand the high heat and moisture content of the pelleting process, but subsequently dissolve in the lower temperature and higher moisture conditions, e.g., in the animal's gut.

Another option is to use intrinsically thermostable phytases. These phytases can theoretically be derived from thermophilic and hyperthermophilic organisms and have unique structure and function properties of high thermostability. However, these phytases may suffer from other limitations, like suboptimal activity, specificity, bioavailability, pH-range or processability.

It is hence one object of the present invention to provide stable phytase variants which do not suffer from the above discussed limitations.

SUMMARY OF THE INVENTION

These and further objects are met with methods and means according to the independent claims of the present invention. The dependent claims are related to specific embodiments.

BRIEF DESCRIPTION OF THE FIGURES

FIG. 1: Structure of Phytate

FIG. 2: Scheme depicting the reaction catalysed by phytase

FIG. 3: Synopsis showing properties of some selected synthetic (shuffled) phytase enzymes according to the present invention vs the respective wildtype (reference) phytases. See examples 2-5 for the respective experimental description. In one embodiment of the invention, thermostability may have priority over protease stability or pH stability. This means that in case that, in a given shuffling product, a substantial increase in IT50 is achieved, slight losses in protease stability or pH stability may be acceptable (e.g., losses of −10 or −20%). See for example, OHO, which has a superior thermostability (IT50), yet a slightly reduced resistance against pepsin digestion.

FIG. 4: Two schemes depicting the shuffling process and the optional subsequent mutagenesis FIG. 5: Alignment of the amino acid sequences of the phytases of *Hafnia alvei* (SEQ ID NO 1) and *Obesumbacterium proteus* (SEQ ID NO 2), representing a sequence identity of 73.8%. Beside *Obesumbacterium proteus*, further bacterial phytases are evolutionary close to the phytase of *Hafnia alvei* and fall within the same scope of identity. These similar phytases belong to the family of Enterobacteriaceae and contain both bacteria of the genus *Buttiauxella* and bacteria of the species *E. coli*. Out of these evolutionary close phytases, the phytase of *Obesumbacterium proteus* was specifically selected for the shuffling process with the phytase of *Hafnia alvei.*

FIG. 6: Alignment of the amino acid sequences of the phytase of *Hafnia alvei* (SEQ ID NO 1) and the shuffling product OHO (SEQ ID NO 3). The underlined amino acids represent biobricks taken from *Obesumbacterium proteus*, while the bold printed amino acids represent biobricks taken from *Hafnia alvei.*

EMBODIMENTS OF THE INVENTION

Figure 7:
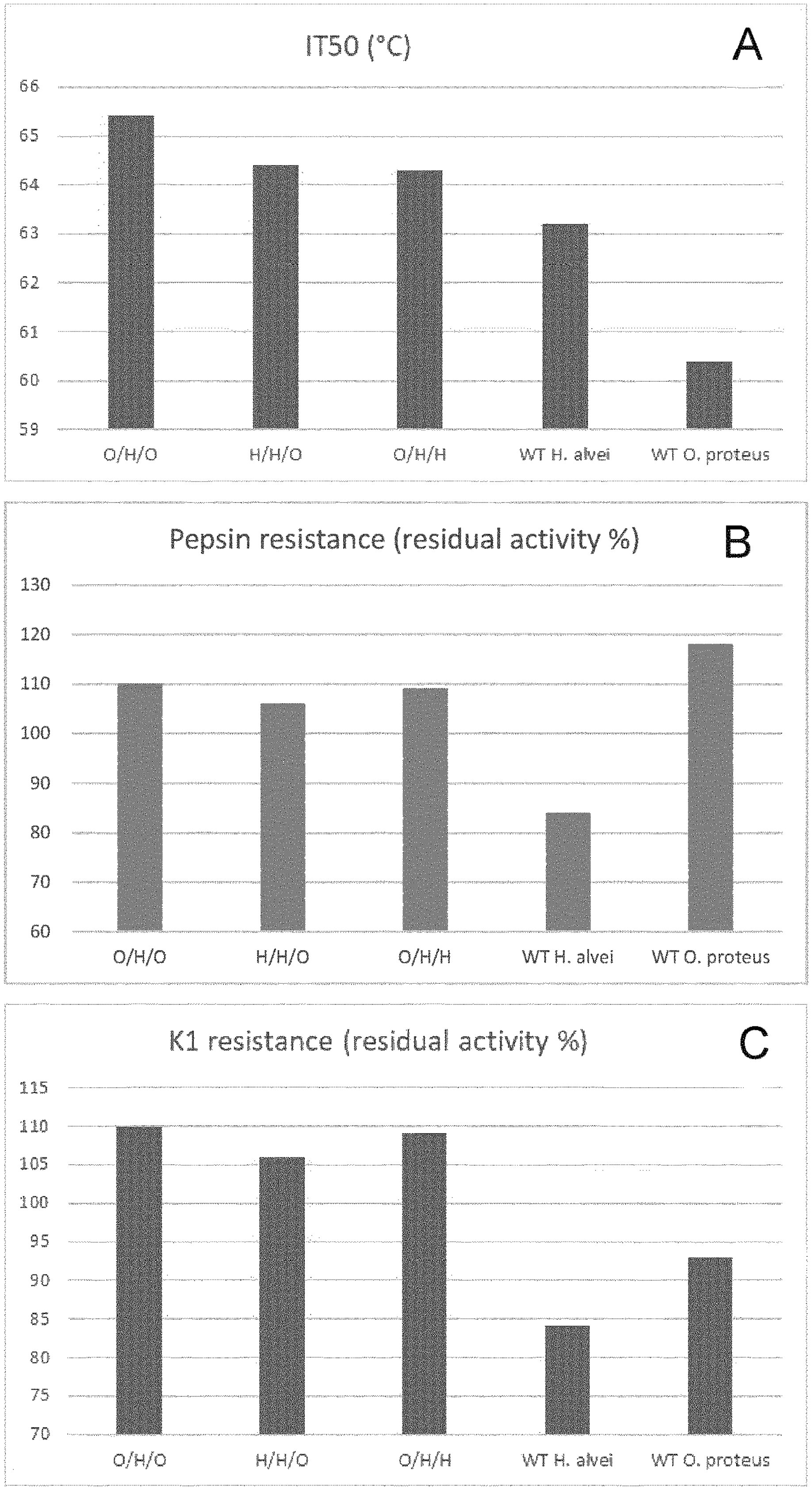
FIG. 7: Graphical illustration of the results of the experiments shown in FIG. 3

Before the invention is described in detail, it is to be understood that this invention is not limited to the particular component parts or structural features of the devices or compositions described or process steps of the methods described as such devices and methods may vary. It is also to be understood that the terminology used herein is for purposes of describing particular embodiments only, and is not intended to be limiting. The mere fact that certain measures are recited in mutually different dependent claims does not indicate that a combination of these measures cannot be used to advantage. Any reference signs in the claims should not be construed as limiting the scope. It must be noted that, as used in the specification and the appended claims, the singular forms “a,” “an” and “the” include singular and/or plural referents unless the context clearly dictates otherwise. Further, in the claims, the word “comprising” does not exclude other elements or steps.

It is moreover to be understood that, in case parameter ranges are given which are delimited by numeric values, the ranges are deemed to include these limitation values.

It is further to be understood that embodiments disclosed herein are not meant to be understood as individual embodiments which would not relate to one another. Features discussed with one embodiment are meant to be disclosed also in connection with other embodiments shown herein. If, in one case, a specific feature is not disclosed with one embodiment, but with another, the skilled person would understand that does not necessarily mean that said feature is not meant to be disclosed with said other embodiment. The skilled person would understand that it is the gist of this application to disclose said feature also for the other embodiment, but that just for purposes of clarity and to keep the specification in a manageable volume this has not been done.

According one aspect of the invention, a synthetic phytase is provided which is a shuffling product comprising biobricks of at least two reference phytases of *Obesumbacterium* and/or *Hafnia.*

The inventors have found out that the phytases of *Obesumbacterium* and *Hafnia* turned out to be the highly promising starting points (domain structure, sequence similarity, and the like) to obtain functional shuffling constructs wot potentially increased stability, based on a molecular modeling process as disclosed elsewhere herein.

The term “biobricks”, as used herein, relates to standardized building bricks consisting of DNA sequences that are fragments of a larger DNA, cDNA, RNA or mRNA sequence encoding for proteins with a specific and defined function. “Biobricks” exhibit the same cutting sites, wherefore they are easy to combine. Here, the used DNA sequences encode for a phytase enzyme and are used as building blocks to reassemble a synthetic, “shuffled” DNA encoding for a synthetic, “shuffled”, phytase enzyme. More precisely, DNA sequences of *Obesumbacterium* and/or *Hafnia* encoding for the respective phytase enzyme are used as building blocks and are reassembled to a synthetic “shuffled” phytase enzyme.

The term “reference phytase”, as used herein, relates to a DNA, cDNA, RNA or mRNA sequence encoding for a phytase enzyme that is being used as the starting point of the method, as the source for such biobricks, or to the phytase enzyme encoded thereof.

A “shuffling product”, as used herein, is an enzyme which consists of two or more such biobricks from at least two different reference phytases. In the shuffling product, the biobricks from the different reference phytases have been reassembled in a specific or random order, in order to modify the characteristics of the reference phytases.

In one embodiment, the different reference phytases have been fragmented to obtain biobricks of corresponding function, orientation in the reference phytases and/or similar length.

For example, fragmentation of reference phytase A delivers biobricks 1, 2 and 3, while fragmentation of reference phytase B delivers corresponding biobricks 1', 2' and 3'.

Biobricks 1 and 1', biobricks 2 and 2' and biobricks 3 and 3', respectively, have corresponding function, orientation in the reference phytases and/or similar length, and are hence called “corresponding biobricks”.

In one embodiment, upon reassembly, one member out of each set of corresponding biobricks is selected, and the selected biobricks are combined to reproduce the orientation of the different biobricks in one of the reference phytases like e.g. 1'-2-3, 1-2'-3 or the like.

In one embodiment, the process itself does not introduce “new” amino acids residues or amino acid substitutions which go beyond what is being done in the mere shuffling process. As a consequence, the resulting shuffling product does not comprise “new” amino acids residues or amino acid substitutions which go beyond what is being done in the mere shuffling process.

Enzyme shuffling methods are for example disclosed in Engler et al. (2009), the content of which is incorporated herein by reference.

*Obesumbacterium* and *Hafnia* are both genus of the family Hafniaceae, order Enterobacterales, which are Gram-negative bacteria.

In one embodiment, the reference phytase is a wildtype phytase of *Obesumbacterium* and/or *Hafnia*. In another embodiment, the "reference phytase" is a mutated phytase derived from such a wildtype phytase, e.g., a variant which has at least 1 amino acid substitutions compared to, or at least 80% sequence identity with, such wildtype phytase, while maintaining its phytase activity.

In preferred embodiments, the mutated phytase has ≥81, ≥82, ≥83, ≥84, ≥85, ≥86, ≥87, ≥88, ≥89, ≥90, ≥91, ≥92, ≥93, ≥94, ≥95, ≥96, ≥97, ≥98, most preferably ≥99% sequence identity with such wildtype phytase.

In preferred embodiments, the mutated phytase has 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82 or 83 amino acid substitutions compared to such wildtype phytase.

According to one embodiment, at least one reference phytase is, or is derived from, a wildtype phytase of, *Hafnia alvei* and/or *Obesumbacterium proteus*.

The term "derived from" relates to an enzyme variant which has at least 1 amino acid substitutions compared to, or at least 80% sequence identity with, such wildtype phytase, while maintaining its phytase activity.

In preferred embodiments, the enzyme variant has ≥81, ≥82, ≥83, ≥84, ≥85, ≥86, ≥87, ≥88, ≥89, ≥90, ≥91, ≥92, ≥93, ≥94, ≥95, ≥96, ≥97, ≥98, most preferably ≥99% sequence identity with such wildtype phytase.

In preferred embodiments, the enzyme variant has 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82 or 83 amino acid substitutions compared to such wildtype phytase.

According to one embodiment, at least one reference phytase comprises at least one of a) an amino acid sequence according to SEQ ID NO 1 or 2 ("wildtype phytase")
b) the amino acid sequence according to option a), with the proviso that the sequence has at least 1 amino acid substitution relative to the respective SEQ ID NO as specified in a), while maintaining its phytase activity,
c) the amino acid sequence according to option a), with the proviso that the sequence has a sequence identity of at least 80% relative to the respective SEQ ID NO as specified in a), while maintaining its phytase activity.

In preferred embodiments, the enzyme variant has ≥81, ≥82, ≥83, ≥84, ≥85, ≥86, ≥87, ≥88, ≥89, ≥90, ≥91, ≥92, ≥93, ≥94, ≥95, ≥96, ≥97, ≥98, most preferably ≥99% sequence identity relative to the respective SEQ ID NO as specified in a).

In preferred embodiments, the enzyme variant has 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82 or 83 amino acid substitutions relative to the respective SEQ ID NO as specified in a).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (e.g., a polypeptide), which does not comprise additions or deletions, for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same sequences. Two sequences are "substantially identical" if two sequences have a specified percentage of amino acid residues or nucleotides that are the same (i.e., at least 85%, 90%, 95%, 96%, 97%, 98% or 99% sequence identity over a specified region, or, when not specified, over the entire sequence of a reference sequence), when compared and aligned for maximum correspondence over a comparison window, or designated region as measured using one of the following sequence comparison algorithms or by manual alignment and visual inspection.

One suitable algorithm to determine sequence identities is the BLAST algorithm. Another algorithm to determine sequence identities is the Clustal Omega algorithm.

The disclosure provides polypeptides or polynucleotides that are substantially identical to the polypeptides or polynucleotides, respectively, exemplified herein. Optionally, the identity exists over a region that is at least about 15, 25 or 50 nucleotides in length, or more preferably over a region that is 100 to 500 or 1000 or more nucleotides in length, or over the full length of the reference sequence. With respect to amino acid sequences, identity or substantial identity can exist over a region that is at least 5, 10, 15 or 20 amino acids in length, optionally at least about 25, 30, 35, 40, 50, 75 or 100 amino acids in length, optionally at least about 150, 200 or 250 amino acids in length, or over the full length of the reference sequence. With respect to shorter amino acid sequences, e.g., amino acid sequences of 20 or fewer amino acids, substantial identity exists when one or two amino acid residues are conservatively substituted, according to the conservative substitutions defined herein.

According to one or more embodiments of the invention, at least one amino acid substitution as discussed above is a conservative amino acid substitution.

A "conservative amino acid substitution" has a smaller effect on enzyme function than a non-conservative substitution. Although there are many ways to classify amino acids, they are often sorted into six main groups on the basis of their structure and the general chemical characteristics of their R groups.

In one embodiment, a "conservative amino acid substitution" is one in which the amino acid residue is replaced with an amino acid residue having a similar side chain. For example, families of amino acid residues having similar side chains have been defined in the art. These families include amino acids with basic side chains (e.g., lysine, arginine, histidine),
acidic side chains (e.g., aspartic acid, glutamic acid),
uncharged polar side chains (e.g., glycine, asparagine, glutamine, serine, threonine, tyrosine, cysteine),
nonpolar side chains (e.g., alanine, valine, leucine, isoleucine, proline, phenylalanine, methionine, tryptophan),
beta-branched side chains (e.g., threonine, valine, isoleucine) and
aromatic side chains (e.g., tyrosine, phenylalanine, tryptophan, histidine).

Other conserved amino acid substitutions can also occur across amino acid side chain families, such as when substituting an asparagine for aspartic acid in order to modify the charge of a peptide. Thus, a predicted nonessential amino acid residue in a HR domain polypeptide, for example, is preferably replaced with another amino acid residue from the same side chain family or homologues across families (e.g. asparagine for aspartic acid, glutamine for glutamic acid). Conservative changes can further include substitution of chemically homologous non-natural amino acids (i.e. a synthetic non-natural hydrophobic amino acid in place of leucine, a synthetic non-natural aromatic amino acid in place of tryptophan).

As used herein, the term "maintaining its phytase activity" means, for example, that the respective variant has a phytase activity of ≥50% compared to that of the wildtype phytase sequence.

According to one embodiment, the synthetic phytase has one of the following shuffling structures shown in N->C direction:

O/H/O

H/H/O, and/or

O/H/H wherein O stands for a biobrick from the *Obesumbacterium* reference phytase, and H stands for a biobrick from the *Hafnia* reference phytase.

The following table gives an overview of preferred building block lengths:

| | start of SEQ ID No 1 | end or 2 | Length (AA) |
|---|---|---|---|
| N-terminal biobrick | 1 | 107 | 107 |
| middle biobrick | 108 | 264 | 157 |
| C-terminal biobrick | 265 | 411-413 | 147-149 |

According to one embodiment, the synthetic phytase comprises one of a) an amino acid sequence according to any one of SEQ ID NO 3-5 ("shuffled sequence")

b) the amino acid sequence according to option a), with the proviso that the sequence has at least 1 amino acid substitutions relative to the respective SEQ ID NO as specified in a), while maintaining its phytase activity, c) the amino acid sequence according to option a), with the proviso that the sequence has a sequence identity of ≥80% relative to the respective SEQ ID NO as specified in a), while maintaining its phytase activity.

The above-mentioned synthetic phytases are shuffling products comprising biobricks from the *Obesumbacterium* reference phytase and the *Hafnia* reference phytase. Surprisingly, the generated synthetic phytases were increased in their thermostability ($IT_{50}$) compared to their reference phytases. Although the $IT_{50}$ value of the *Hafnia* reference phytase is about 63° C. and the $IT_{50}$ value of the *Obesumbacterium* reference phytase is about 60° C., all three shuffling products exceed the thermostability of the *Hafnia* reference phytase and did not demonstrate a mean value of the $IT_{50}$ values.

In preferred embodiments, the enzyme variant has ≥81, ≥82, ≥83, ≥84, ≥85, ≥86, ≥87, ≥88, ≥89, ≥90, ≥91, ≥92, ≥93, ≥94, ≥95, ≥96, ≥97, ≥98, most preferably ≥99% sequence identity relative to the respective SEQ ID NO as specified in a).

In preferred embodiments, the enzyme variant has 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82 or 83 amino acid substitutions relative to the respective SEQ ID NO as specified in a).

According to one or more embodiments of the invention, at least one amino acid substitution as discussed above is a conservative amino acid substitution.

According to one embodiment, the synthetic phytase has an increased stability compared to one of the reference phytases.

According to one embodiment, said increased stability is increased thermostability ($IT_{50}$) compared to one of the reference phytases.

Note, in this context, that the IT50 of the reference phytases are as follows:

| | |
|---|---|
| Hafnia alvei appA | 63° C. |
| Obesumbacterium proteus appA | 60° C. |

The term "thermostability" as used herein refers to the ability of an enzyme to have equal or greater activity compared to the wild type under standard conditions, and an increased ability to retain activity after exposure to increased temperatures.

According to one embodiment, the synthetic phytase has an $IT_{50}$ of ≥60° C. According to further embodiments, the synthetic phytase has an $IT_{50}$ of ≥65° C., ≥70° C., ≥75° C., ≥80° C., or ≥85° C.

According to one embodiment, the synthetic phytase has an $IT_{50}$ of ≤110° C. According to further embodiments, the synthetic phytase has an $IT_{50}$ of ≤105° C.; ≤100° C.; or ≤98° C.

According to one embodiment, the synthetic phytase has an $IT_{50}$ of between ≥60° C. and ≤110° C. According to further embodiments, the synthetic phytase has an $IT_{50}$ of between ≥65° C. and ≤105° C., between ≥70° C. and ≤100° C., between ≥75° C. and ≤98° C. between ≥80° C. and ≤98° C. or between ≥85° C. and ≤98° C.

According to one embodiment, said increased stability is increased stability against protease digestion (also called "protease resistance") compared to one of the reference phytases.

The stability against protease digestion can be measured by exposure to the protease K1 (Kumamolisin AS1, as described in WO2017220776A1). Such stability is quite important because very often phytases are combined with proteases and then used in a specific purpose. Hence, the risk exists that the protease will deactivate, or even digest, the concomitantly added phytase.

In addition or as an alternative, the stability against protease digestion can be measured by exposure to the protease pepsin. Such stability is quite important because when used in feed applications, the phytase will have to survive and be active in the gastric environment where pepsin is present and active. Hence, the risk exists that the protease will deactivate, or even digest, the concomitantly added phytase.

As a result of any enzyme optimization process, the optimization of one parameter can affect other parameters. For example, increasing thermostability can at the same time also increase or reduce protease stability or pH stability.

In the present case of a phytase for animal feed purposes, in one embodiment, thermostability may have priority over protease stability or pH stability. This means that in case that, in a given shuffling product, a substantial increase in IT50 is achieved, slight losses in protease stability or pH stability may be acceptable (e.g., losses of −10 or −20%).

According to one embodiment, said increased stability is increased pH stability (also called "pH resistance") compared to one of the reference phytases.

The term "pH stability" as used herein refers to the ability of an enzyme to have equal or greater activity compared to the wild type under standard conditions, and an increased ability to retain activity after exposure to acidic conditions (e.g., pH 4.0 or lower).

According to one other aspect of the invention, a nucleic acid molecule is provided which encodes a synthetic phytase according to the above description.

In one embodiment, such nucleic acid molecule is codon optimized for the expression in eukaryotic hosts, preferably from the group of yeasts and fungi, most preferably for *Pichia pastoris, Aspergillus* sp. and *Trichoderma* sp.

Codon optimization is a useful technology for improving the expression of heterologous proteins. Indeed, there is a large difference between the codon usage of the host cell genome sequence and the native heterologous protein encoding sequence, which will obviously affect the expression of recombinant proteins. Some reports have shown that the production of the target proteins was often increased an average of 1- to 5-fold by optimizing the heterologous protein-encoding sequence based on the codon bias of the host cell.

Codon optimization is a species-specific process, and the skilled artisan is able to derive, from respective literature reference, suitable codon optimizations schemes for a given expression host. Respective teachings are provided, e.g., in Yu et al (2013), Rosemary et al (2017) and Yang and Liu (2010), the contents of which are incorporated herein by reference for enablement purposes.

According to one other aspect of the invention, a plasmid or vector system comprising the nucleic acid molecule is provided.

According to one other aspect of the invention, a host cell capable of heterologous protein expression is provided, said host cell comprising a plasmid or vector system comprising the nucleic acid molecule according to the above description.

According to yet one other aspect of the invention, the heterologous protein expression is achieved by insertion of the said nucleic acid molecule into the genome of the said host cell. The genomic insertion is achieved using homologous recombination based state-of-the-art techniques and genome-editing using programmable nucleases, e.g. CRISPR-Cas, Zn-finger or TAL endonucleases.

In different embodiments, such host cell is at least one selected from a bacterial cell, fungal cell or a yeast cell.

Exemplary bacterial cells include *E. coli* and other Enterobacteriaceae, *Escherichia* sp., *Campylobacter* sp., *Wolinella* sp., *Desulfovibrio* sp., *Vibrio* sp., *Pseudomonas* sp. *Bacillus* sp., *Bacteroides* sp., *Listeria* sp., *Staphylococcus* sp., *Streptococcus* sp., *Peptostreptococcus* sp., *Megasphaera* sp., *Pectinatus* sp., *Selenomonas* sp., *Zymophilus* sp., *Actinomyces* sp., *Arthrobacter* sp., *Frankia* sp., *Micromonospora* sp., *Nocardia* sp., *Propionibacterium* sp., *Streptomyces* sp., *Lactobacillus* sp., *Lactococcus* sp., *Leuconostoc* sp., *Pediococcus* sp., *Acetobacterium* sp., *Agrobacterium* sp., *Aliivibrio* sp., *Eubacterium* sp., *Haloarcula* sp., *Halobacterium* sp., *Heliobacterium* sp., *Heliospirillum* sp., *Sporomusa* sp., *Spiroplasma* sp., *Ureaplasma* sp., *Erysipelothrix*, sp., *Corynebacterium* sp. *Enterococcus* sp., *Clostridium* sp., *Mycoplasma* sp., *Mycobacterium* sp., *Actinobacteria* sp., *Salmonella* sp., *Shigella* sp., *Moraxella* sp., *Helicobacter* sp, *Paracoccidioides* sp., *Stenotrophomonas* sp., *Micrococcus* sp., *Neisseria* sp., *Bdellovibrio* sp., *Hemophilus* sp., *Thermus* sp., *Klebsiella* sp., *Proteus* sp., *Enterobacter* sp., *Serratia* sp., *Citrobacter* sp., *Pseudomonas* sp., *Proteus* sp., *Rhodobacter* sp., *Rhodopseudomonas* sp., *Rhodospirillum* sp., *Serratia* sp., *Yersinia* sp., *Acinetobacter* sp., *Actinobacillus* sp. *Bordetella* sp., *Brucella* sp., *Capnocytophaga* sp., *Cardiobacterium* sp., *Eikenella* sp., *Francisella* sp., *Haemophilus* sp., *Kingella* sp., *Pasteurella* sp., *Flavobacterium* sp. *Xanthomonas* sp., *Burkholderia* sp., *Aeromonas* sp., *Plesiomonas* sp., *Legionella* sp. and alpha-proteobacteria such as *Wolbachia* sp., Comamonas sp., *Pyrobaculum* sp., *Sinorhizobium* sp., *Cyanobacteria, spirochaetes*, green sulfur and green non-sulfur bacteria, Gram-negative cocci, Gram negative bacilli. In a preferred embodiment the bacterial cell is *Bacillus subtilis.*

Exemplary fungi or yeast cells include *Pichia* sp., *Aspergillus* sp., *Kluyveromyces* sp., *Saccharomyces* sp., *Candida* sp., *Trichoderma* sp., *Penicillium* sp., *Neurospora* sp., *Chrysosporium* sp., *Cladosporium* sp., *Phytophthora* sp., *Scytalidium* sp., more preferred *Saccharomyces cerevisiae, Pichia pastoris, Aspergillus nidulans, Aspergillus niger, Trichoderma reesei, Kluyveromyces lactis, Kluyveromyces marxianus*, and *Neurospora crassa.*

In a preferred embodiment the yeast cell is *Pichia pastoris*. This methanol utilizing yeast is a widely used eukaryotic production host for the expression of recombinant proteins, known also as *Konagataella phaffii.*

In further embodiments, such host cell is a eukaryotic host cell selected from the group consisting of plant cells, insect cells or mammalian cells.

According to one other aspect of the invention, a feed additive, feed ingredient, feed supplement, and/or feedstuff comprising a synthetic phytase according to the above description is provided.

According to one other aspect of the invention, the use of a synthetic phytase according to the above description is provided for the manufacture of a feedstuff.

According to one other aspect of the invention, a process of developing a synthetic phytase according to the above description is provided, which process comprises:

a) providing two or more DNA, cDNA, RNA or mRNA sequences encoding for at least two reference phytases from *Obesumbacterium* and/or *Hafnia,*
b) digesting the two or more DNA, cDNA, RNA or mRNA sequences by means of a type II restriction enzyme, to create DNA, cDNA, RNA or mRNA stretches that are fragments of the DNA, cDNA, RNA or mRNA sequences of step a)
c) ligating the DNA, cDNA, RNA or mRNA substretches by means of a ligase enzyme, so as to create at least one shuffled DNA, cDNA, RNA or mRNA sequence encoding for a shuffled phytase enzyme, and
d) optionally, expressing said shuffled DNA, cDNA, RNA or mRNA sequence in a suitable expression system.

In one embodiment, steps b)-c) are repeated two or more times.

The type II restriction enzyme is preferably a type IIS restriction enzyme, preferably BsaI, BsmBI, and BbsI. Unlike standard Type II restriction enzymes like EcoRI and BamHI, these enzymes cut DNA outside of their recognition sites and, therefore, can create non-palindromic overhangs. Since 256 potential overhang sequences are possible, multiple fragments of DNA can be assembled by using combinations of overhang sequences.

The ligase is preferably a T4 DNA ligase.

The restriction step b) is preferably carried out a temperature of 35-40° C. (preferably, 37° C.), while the ligation step c) is preferably carried out a temperature of 10-20° C. (preferably, 16° C.).

In one embodiment, the process is carried in a thermal cycler, with a protocol that oscillates between, e.g., 37° C. (for restriction) and, e.g., 16° C. (for ligation) many times.

According to one embodiment, the process further comprises e) mutagenizing a DNA, cDNA, RNA or mRNA sequence encoding for a shuffled phytase enzyme according to the above description, to obtain one or more mutated phytase sequences, f) expressing one or more mutated phytase sequences thus obtained, in a suitable expression system, to obtain one or more mutated phytase enzymes, and g) testing the one or more mutated phytase enzymes sequences for stability, preferably thermostability.

Experiments and Figures

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. Any reference signs should not be construed as limiting the scope. All amino acid sequences disclosed herein are shown from N-terminus to C-terminus; all nucleic acid sequences disclosed herein are shown 5'->3'.

Example 1: Designing Semi-Rational Libraries of Shuffled Enzymes

Phytases belonging to the same protein family, based on a multiple structure-based alignment of the histidine acid phytase superfamily employing the 3DM system (Bio Prodict, Nijmegen. NL), and having different beneficial traits, were clustered. This phytase cluster was analyzed for potential fragmentation sites. These fragmentation sites were selected to be at amino acid positions conserved in all proteins of the cluster, being outside helices and B-sheets and being a proline or in close proximity to a proline (3 amino acids). Libraries consisted of at least two proteins and at last two preferably more, fragments, called biobricks.

In this process, the phytases of *Obesumbacterium* and *Hafnia* turned out to be the most promising starting points (domain structure, sequence similarity, and the like) to obtain functional shuffling constructs with potentially increased stability.

The biobricks are generated by PCR introducing Type IIs restriction sites that generate sequence-specific overhangs. Recombination of these biobricks maintained the sequence of the structural elements and does not introduce amino acid changes to the biobricks or extra amino acids. The procedure further ensured that none of the biobricks from different parent backbones is discriminated or preferentially integrated, so that all possible combinations can be obtained by the process.

The method can be generally used to recombine homologous proteins with each other. At least one of the proteins should have a solved crystal structure, from which the structure of the homologous proteins can be derived via a homology comparison, such as a structure based alignment.

In the recombination of different bacterial phytases, three domains were selected. Prolines, which terminate the selected protein domains, were selected as recombination sites.

Example 2: Phytase Activity Assay

Assay buffer: 100 mM Na-Acetate pH 5.5
10 mM sodium phytate
5 mM $CaCl_2$)
Stop solution: 20% (w/v) trichloroacetic acid (TCA)
Color reagent solution: 1 part iron sulfate solution (388 mM $FeSO_4 \times 7H_2O$ in 2.5 N $H_2SO_4$)
4 parts ammonium molybdate solution
(12 mM $(NH_4)_6Mo_7O_{24} \times 4H_2O$ in 2.5 N $H_2SO_4$)

Samples were diluted in $ddH_2O$ containing 0.01% Triton-X-100 according to their volumetric activity. Diluted samples were than assayed in Nunc 384 well clear flat bottom plate. The reaction was started by adding 1 part assay buffer to one part diluted sample and incubation at 37° C. for 30 min in a thermoshaker. The reaction was subsequently stopped by adding an equal volume of stop solution. The color reaction was started by adding an equal volume of color reagent solution and incubation at 25° C. in the dark for 20 minutes. The absorbance at 650 nm was measured and the amount of phosphate liberated by the phytase was evaluated against an inorganic phosphate standard curve measured under the same conditions.

Example 3: IT50

IT50 defines the temperature where 50% of the activity is inactivated under the conditions described below. Although not equivalent to, it is a measure for the thermal stability in the application, e.g. pelleting conditions.

Thermal incubation buffer: 100 mM Na-Acetate pH 5.5
0.5 mg $mL^{-1}$ digested BSA
5 mM $CaCl_2$)
0.01% Triton-X-100

The supernatants of submerse cultivation of bacterial or fungal strains producing the phytase or phytase variant of interest were diluted in thermo incubation buffer. Aliquots of 50 μl were incubated for 10 minutes in a PCR machine at an appropriate thermal gradient. A second aliquot was incubated at 25° C. After the thermal incubation the sample is kept at 25° C. and assayed for residual activity by the phytase activity assay described under example 2. Results are shown in the table/FIG. 3 and FIG. 7A.

Example 4: pH Activity Profile

Dilution buffer: 0.5 mg $mL^{-1}$ digested BSA
0.001% Triton-X-100
Assay buffer pH 2.0-3.5: 250 mM Glycin-HCl
5.6 mM phytate
5.6 mM $CaCl_2$
Assay buffer pH 4.0-5.5: 250 mM sodium acetate
5.6 mM phytate
5.6 mM $CaCl_2$)
Assay buffer pH 6.0-7.0: 250 mM MES
5.6 mM phytate
5.6 mM $CaCl_2$)

Supernatant of submerse cultivation of bacterial or fungal strains producing the phytase or phytase variant of interest were diluted according to their volumetric activity in dilution buffer. The activity was measured according to the assay described under example 1, with modification of the assay buffers for the required pH. The reaction was started by adding 8 parts of one of the above buffers to provide activity measurements at ambient pH from pH 2.0 to 7.0. The reaction was stopped and inorganic phosphate was measured as described in example 2. Results are shown in the table/FIG. 3.

Example 5: pH/Pepsin/K1 Stability

The procedure provides information about the resistance against acid proteases, as residual activity. Acid proteases tested are pepsin and the acid protease Kumamolisin AS (K1; see for example European patent publications EP16206367, EP16176044, the contents of which are incorporated herein by reference) as a representative for the acid protease of the protease families S53 and G1.

pH 2.5 assay buffer: 100 mM Glycine-HCl pH 2.5
- 5 mg $mL^{-1}$ digested BSA
- 10 mM $CaCl_2$)

pH2.5/Pepsin Assay: 100 mM Glycine-HCl pH 2.5
- 0.5 mg $mL^{-1}$ pepsin
- 5 mg $mL^{-1}$ digested BSA
- 10 mM $CaCl_2$)

pH 2.5 Kumamolisin AS Assay: Glycine-HCl pH 2.5
- 12 U $mL^{-1}$ Kumamolisin As
- 5 mg $mL^{-1}$ digested BSA
- 10 mM $CaCl_2$ One part of the supernatants of submerse cultivation of bacterial or fungal strains producing the phytase or phytase variant of interest were diluted with 1 one part of the above buffers, to test for the stability against acid pH, acid pH and pepsin or acid pH and protease K1. Assays were incubated for 30 minutes at 37° C. The residual activity is measured immediately after the incubation as described in example 2. Results are shown in the table/FIG. 3 and FIG. 7A.

REFERENCES

The content of the prior art documents referred to herein is incorporated by reference. This refers, particularly, for prior art documents that disclose standard or routine methods. In that case, the incorporation by reference has mainly the purpose to provide sufficient enabling disclosure, and avoid lengthy repetitions.

Engler C et al., Golden Gate Shuffling: A One-Pot DNA Shuffling Method Based on Type IIs Restriction Enzymes. PLoS One. 2009; 4(5): e5553

Yu, P et al., Codon optimisation improves the expression of *Trichoderma viride* sp. endochitinase in *Pichia pastoris*. Sci Rep 3, 3043 (2013).

Rosemary A. Cripwell et al., Expression and comparison of codon optimised *Aspergillus tubingensis* amylase variants in *Saccharomyces cerevisiae*, FEMS Yeast Research, Volume 17, Issue 4, June 2017, fox040

Jiangke Yang, Liying Liu, Codon optimization through a two-step gene synthesis leads to a high-level expression of *Aspergillus niger* lip2 gene in *Pichia pastoris*, Journal of Molecular Catalysis B: Enzymatic, Volume 63, Issues 3-4, May 2010, Pages 164-169

Partridge G, New generation phytase with high thermostability. Pig Progress Vol 23 (4) 2007

SEQUENCE LISTING

The following sequences form part of the disclosure of the present application. A WIPO ST 25 compatible electronic sequence listing is provided with this application, too. For the avoidance of doubt, if discrepancies exist between the sequences in the following table and the electronic sequence listing, the sequences in this table shall be deemed to be the correct ones.

| No | Qualifier | Sequence |
|---|---|---|
| 1 | *Hafnia alvei* wildtype (reference phytase) | SDTAPAGFQLEKVVILSRHGVRAPTKMTQTMRNVTPHQWPEWPVKLGY<br>ITPRGEHLISLMGGFYRERFQQQGLLPKDNCPTPDAVYVWADVDQRTR<br>KTGEAFLAGLAPQCDLAIHHQQNIQQADPLFHPVKAGICSMDKSQAHA<br>AVEKQAGTPIETLNQRYQASLALMSSVLDFPKSPYCQQHNIGKLCDFS<br>QAMPSRLAINDDGNKVALEGAVGLSSTLAEIFLLEHAQGMPKVAWGNI<br>HTEQQWDSLLKLHNAQFDLMSRTPYIAKHNGTPLLQTIAHALGSNIAS<br>RPLPDISPDNKILFIAGHDTNIANISGMLGMTWTLPGQPDNTPPGGAL<br>VFERWVDNAGKPYVSVNMVYQTLAQLHDQTPLTLQHPAGSVRLNIPGC<br>SDQTPDGYCPLSTFSRLVNHSVEPACQLP |
| 2 | Obesumbacterium wildtype (reference phytase) | SETVPSGYQLEKVVILSRHGVRAPTKMTQTMRDVTPNTWPEWPVKLGY<br>ITPRGEHLVSLMGGFYRQKFQQLGILSKDRCPTANDVYVWADVDQRTR<br>KTGEAFLAGLAPECHLSIHHQQDIKQVDSLFHPVKAGVCTMEKAQVQQ<br>AVEQQAGMPIAQLNQHYRPALALMSNVLNFPTSAYCQQHSAEQTCNFA<br>EVMPSKLSIKDDGNKVALDGAVGLSSTLAEIFLLEHAQGMPNAAWGKI<br>HSEQDWNTLLTLHNAQFDLMSRTPYIAKHNGTPLLQTIVSAINSQTSP<br>RELPELSADNKILFLAGHDTNIANIAGMLGLSWTLPGQPDNTPPGGAL<br>VFERWSDKTGKKYVSAQMMYQTLAQLRNQTPLTLDEPAGSVALKIPGC<br>DDQTAEGYCPLDTFTRLAKQNELAECQ |
| 3 | Shuffled variant "OHO" | SETVPSGYQLEKVVILSRHGVRAPTKMTQTMRDVTPNTWPEWPVKLGY<br>ITPRGEHLVSLMGGFYRQKFQQLGILSKDRCPTANDVYVWADVDQRTR<br>KTGEAFLAGLAPQCDLAIHHQQNIQQADPLFHPVKAGICSMDKSQAHA<br>AVEKQAGTPIETLNQRYQASLALMSSVLDFPKSPYCQQHNIGKLCDFS<br>QAMPSRLAINDDGNKVALEGAVGLSSTLAEIFLLEHAQGMPKVAWGNI<br>HTEQQWDSLLKLHNAQFDLMSRTPYIAKHNGTPLLQTIVSAINSQTSP<br>RELPELSADNKILFLAGHDTNIANIAGMLGLSWTLPGQPDNTPPGGAL<br>VFERWSDKTGKKYVSAQMMYQTLAQLRNQTPLTLDEPAGSVALKIPGC<br>DDQTAEGYCPLDTFTRLAKQNELAECQ |

-continued

| No | Qualifier | Sequence |
|---|---|---|
| 4 | Shuffled variant "HHO" | SDTAPAGFQLEKVVILSRHGVRAPTKMTQTMRNVTPHQWPEWPVKLGY ITPRGEHLISLMGGFYRERFQQQGLLPKDNCPTPDAVYVWADVDQRTR KTGEAFLAGLAPQCDLAIHHQQNIQQADPLFHPVKAGICSMDKSQAHA AVEKQAGTPIETLNQRYQASLALMSSVLDFPKSPYCQQHNIGKLCDFS QAMPSRLAINDDGNKVALEGAVGLSSTLAEIFLLEHAQGMPKVAWGNI HTEQQWDSLLKLHNAQFDLMSRTPYIAKHNGTPLLQTIVSAINSQTSP RELPELSADNKILFLAGHDTNIANIAGMLGLSWTLPGQPDNTPPGGAL VFERWSDKTGKKYVSAQMMYQTLAQLRNQTPLTLDEPAGSVALKIPGC DDQTAEGYCPLDTFTRLAKQNELAECQ |
| 5 | Shuffled variant "OHH" | SETVPSGYQLEKVVILSRHGVRAPTKMTQTMRDVTPNTWPEWPVKLGY ITPRGEHLVSLMGGFYRQKFQQLGILSKDRCPTANDVYVWADVDQRTR KTGEAFLAGLAPQCDLAIHHQQNIQQADPLFHPVKAGICSMDKSQAHA AVEKQAGTPIETLNQRYQASLALMSSVLDFPKSPYCQQHNIGKLCDES QAMPSRLAINDDGNKVALEGAVGLSSTLAEIFLLEHAQGMPKVAWGNI HTEQQWDSLLKLHNAQFDLMSRTPYIAKHNGTPLLQTIAHALGSNIAS RPLPDISPDNKILFIAGHDTNIANISGMLGMTWTLPGQPDNTPPGGAL VFERWVDNAGKPYVSVNMVYQTLAQLHDQTPLTLQHPAGSVRLNIPGC SDQTPDGYCPLSTFSRLVNHSVEPACQLP |

What is claimed is:

1. A synthetic phytase which is a shuffling product comprising biobricks of at least two reference phytases of Obesumbacterium and/or Hafnia which phytase comprises one of a) the amino acid sequence according to SEQ ID NO 3 ("shuffled sequence"), or b) the amino acid sequence according to option a), with the proviso that the sequence has a sequence identity of ≥90% relative to SEQ ID NO 3 as specified in a), while maintaining its phytase activity.

2. The synthetic phytase according to claim 1, which phytase has an increased stability compared to one of the reference phytases, wherein the reference phytase is, or is derived from, a wildtype phytase of *Hafnia alvei* (SEQ ID NO: 1) or *Obesumbacterium proteus* (SEQ ID NO: 2).

3. The synthetic phytase according to claim 2, wherein said increased stability is increased thermostability ($IT_{50}$) compared to one of the reference phytases.

4. The synthetic phytase according to claim 3, which has an $IT_{50}$ of between ≥60° C. and ≤100° C.

5. The synthetic phytase according to claim 2, wherein said increased stability is increased stability against protease digestion compared to one of the reference phytases.

6. The synthetic phytase according to claim 3, wherein said increased stability is increased pH stability compared to one of the reference phytases.

7. The synthetic phytase according to claim 1, which is encoded by a nucleic acid molecule.

8. The synthetic phytase according to claim 7, wherein the nucleic acid molecules is a plasmid or vector system.

9. A host cell capable of heterologous protein expression, said host cell comprising a plasmid or vector system according to claim 8.

10. A feed additive, feed ingredient, feed supplement, and/or feedstuff comprising a synthetic phytase according to claim 1.

11. A process for the manufacture of a feedstuff comprising the use of a synthetic phytase according to claim 1.

12. A host cell capable of heterologous protein expression, said host cell comprising a nucleic acid molecule according to claim 7.

* * * * *